United States Patent
Miyamoto

(10) Patent No.: US 7,435,243 B2
(45) Date of Patent: Oct. 14, 2008

(54) DISPOSABLE ABSORBENT ARTICLE HAVING BARRIER LEG CUFF AND ELASTICIZED OUTER LEG CUFF

(75) Inventor: Kouichi Miyamoto, Kobe Hyogo (JP)

(73) Assignee: The Procter and Gamble Company, Cincinnati, OH (US)

( * ) Notice: Subject to any disclaimer, the term of this patent is extended or adjusted under 35 U.S.C. 154(b) by 1337 days.

(21) Appl. No.: 10/325,153

(22) Filed: Dec. 20, 2002

(65) Prior Publication Data
US 2003/0120248 A1 Jun. 26, 2003

Related U.S. Application Data

(60) Provisional application No. 60/392,895, filed on Jul. 1, 2002, provisional application No. 60/342,938, filed on Dec. 21, 2001.

(51) Int. Cl.
*A61F 13/20* (2006.01)
(52) U.S. Cl. .................. 604/385.25; 604/385.28; 604/358; 604/378
(58) Field of Classification Search ................ 604/385.25–385.28, 358, 378, 385
See application file for complete search history.

(56) References Cited

U.S. PATENT DOCUMENTS

| | | | | |
|---|---|---|---|---|
| 4,738,677 A | * | 4/1988 | Foreman | 604/385.27 |
| 2002/0029029 A1 | * | 3/2002 | Otsubo | 604/385.101 |
| 2002/0045875 A1 | * | 4/2002 | Minato et al. | 604/385.28 |

FOREIGN PATENT DOCUMENTS

| CA | 1279152 | 1/1991 |
|---|---|---|
| EP | 0 945 111 A2 | 9/1999 |
| EP | 0 978 265 A2 | 2/2000 |
| JP | 02-156946 | 6/1990 |
| JP | 03-207358 A | 9/1991 |
| JP | HEI 4 1992-12751 | 1/1992 |
| JP | 10-277092 | 10/1998 |
| JP | 11-104174 | 4/1999 |
| JP | 2000 079141 | 3/2000 |

* cited by examiner

Primary Examiner—T. Zalukaeva
(74) Attorney, Agent, or Firm—Thibault Fayette; Jay A. Krebs; Matthew P. Fitzpatrick

(57) ABSTRACT

A disposable absorbent article having a barrier leg cuff and an elasticized outer leg cuff is disclosed. The disposable absorbent article comprises a liquid pervious topsheet, a liquid impervious backsheet, an absorbent core disposed therebetween, an elasticized outer leg cuff, and a barrier leg cuff. The elasticized outer leg cuff is disposed adjacent to a longitudinal side edge of the absorbent article. The elasticized outer leg cuff has a base and a gasket cuff supported by the base at a joint of the base to the gasket cuff. The gasket cuff is provided with elasticity and has an inner cuff extending laterally inwardly from the joint and an outer cuff extending laterally outwardly from the joint. The barrier leg cuff is disposed inboard of the gasketing cuff and forms a pocket by a combination of the inner cuff, the base and the barrier leg cuff.

10 Claims, 8 Drawing Sheets

DISPOSABLE ABSORBENT ARTICLE HAVING BARRIER LEG CUFF AND ELASTICIZED OUTER LEG CUFF

CROSS REFERENCE TO RELATED APPLICATIONS

This application claims the benefit of U.S. Provisional Application No. 60/392,895, filed Jul. 1, 2002 and U.S. Provisional Application No. 60/342,938, filed Dec. 21, 2001.

TECHNICAL FIELD

The present invention relates to a disposable absorbent article having a barrier leg cuff and an elasticized outer leg cuff. More specifically, the present invention relates to a disposable absorbent article having a barrier leg cuff disposed inboard of an elasticized outer leg cuff having an inner cuff and an outer cuff.

BACKGROUND

Disposable absorbent articles provided with an elasticized outer leg cuff are well known. There are a number of ways to form an elasticized outer leg cuff. The most common approach is to form the elasticized outer leg cuff from an elastic member being enclosed in the continuous topsheet and the backsheet which extends beyond the edges of the absorbent core. These elasticized outer leg cuffs provide a gasket cuffing action about the legs of the wearer to maintain a seal about the leg and minimize gapping. A number of attempts have been made to further improve an elasticized outer leg cuff to minimize leakage.

Japanese Patent Laid-open publication H04-12751 published on Jan. 17, 1992 discloses an absorbent article comprising a flexible side flap laterally outwardly extending from the longitudinal side edge of the absorbent core and an elastic material disposed on the side flap. The side flap is folded inwardly toward the absorbent core at a portion between the longitudinal side edge of the absorbent core and the inside edge of the elastic material to form a first folding portion, and is folded laterally outwardly at a portion between the first folding portion and the inside edge of the elastic material to form a second folding portion. The second folding portion is joined to the first folding portion in the crotch region to form a T-shaped cuff. It is stated that the second folding portion provides a seal in the crotch region and a pocket formed by the first folding and the second folding portions contain body exudates. European Patent publication 0 346 477 published on Dec. 20, 1989 discloses a disposable nappy comprising a means arranged on opposite sides in the crotch region to prevent leakage. The means comprises a flexible flap and one or more elastic parts. The flap comprises a support section extending up from the nappy, an inner wing section extending inwardly from the support section, and an outer wing section extending outwardly from the support section, in order to provide a T-shaped cuff. However, these publications provide only a single seal around the wearer's leg for primary leakage prevention of body exudates, but does not provide a means for secondary leakage prevention. Further, while the inner edge of the T-shaped cuff contributes for primary leakage prevention of body exudates by its inwardly oriented shape, primary leakage prevention function of the inner edge of the T-shaped cuff becomes deteriorated as the time passes because the inner edge of the T-shaped cuff is always exposed to the body exudates such that the body exudates touches on the inner edge. As a result, the cuffs disclosed in these publications do not provide sufficient leakage prevention effect over long period of wearing time.

European Patent publication 0 945 111 published on Sep. 29, 1999, European Patent publication 0 978 265 published on Feb. 9, 2000, Japanese Patent Laid-open publication 02-156946 published on Jun. 15, 1990 disclose a diaper having a generally T-shaped barrier leg cuff and an elasticized outer leg cuff. The T-shaped barrier leg cuff provides primary leakage prevention of body exudates and the elasticized outer leg cuff provides secondary leakage prevention. While the inner edge of the T-shaped barrier leg cuff enhances primary leakage prevention, primary leakage prevention function of the inner edge of the T-shaped barrier leg cuff becomes deteriorated as the time passes because the inner edge of the T-shaped barrier leg cuff is always exposed to the body exudates such that the body exudates touches on the inner edge. In addition, the elasticized outer leg cuff merely plainly extends outwardly from the proximal edge of the T-shaped barrier leg cuff. Therefore, a pocket to contain the body exudates overflowed the barrier leg cuff can not be effectively formed by the elasticized outer leg cuff and the barrier leg cuff.

Based on the foregoing, there is a need for a disposable absorbent article comprising a barrier leg cuff and an elasticized outer leg cuff comprising a base and a gasket cuff supported by the base. There is also a need for a disposable absorbent article comprising a barrier leg cuff disposed inboard of a gasketing cuff to effectively form a pocket by a gasketing cuff and a barrier leg cuff.

SUMMARY

The present invention is directed to a disposable absorbent article. The disposable absorbent article comprises a liquid pervious topsheet, a liquid impervious backsheet, an absorbent core disposed therebetween, an elasticized outer leg cuff, and a barrier leg cuff. The elasticized outer leg cuff is disposed adjacent to a longitudinal side edge of the absorbent article. The elasticized outer leg cuff has a base and a gasket cuff supported by the base at a joint of the base to the gasket cuff. The gasket cuff is provided with elasticity and has an inner cuff extending laterally inwardly from the joint and an outer cuff extending laterally outwardly from the joint. The barrier leg cuff has a proximal edge and a distal edge. The barrier leg cuff is disposed inboard of the gasketing cuff and the distal edge of the barrier leg cuff is spaced away from the top surface of the topsheet to form a pocket by a combination of the inner cuff, the base and the barrier leg cuff.

All documents cited are, in relevant part, incorporated herein by reference; the citation of any document is not to be construed as an admission that it is prior art with respect to the present invention.

BRIEF DESCRIPTION OF THE DRAWINGS

While the specification concludes with claims particularly pointing out and distinctly claiming the invention, it is believed that the present invention will be better understood from the following description of preferred embodiments taken in conjunction with the accompanying drawings in which:

DETAILED DESCRIPTION

As used herein, the term "absorbent article" refers to devices which absorb and contain body exudates, and more specifically, refers to devices which are placed against or in proximity to the body of the wearer to absorb and contain the various exudates discharged from the body. The term "disposable" is used herein to describe absorbent articles which generally are not intended to be laundered or otherwise restored or reused as an absorbent article (i.e., they are intended to be discarded after a single use and, preferably, to be recycled, composted or otherwise disposed of in an environmentally compatible manner). As used herein, the term "disposed" is used to mean that an element(s) of the diaper is formed (joined and positioned) in a particular place or position as a unitary structure with other elements of the diaper or as a separate element joined to another element of the diaper. As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.) As used herein, the term "diaper" refers to an absorbent article generally worn by infants and incontinent persons about the lower torso. The present invention is also applicable to other absorbent articles such as incontinence briefs, incontinence undergarments, absorbent inserts, diaper holders and liners, feminine hygiene garments, sanitary napkins, pantiliners and the like. The term "longitudinal", as used herein, refers to a line, axis or direction in the plane of the absorbent article that is generally aligned with (e.g., approximately parallel to) a vertical plane which bisects a standing wearer into left and right body halves when the absorbent article is worn. The terms "transverse" or "lateral" used herein, are interchangeable, and refer to a line, axis or direction which lies within the plane of the absorbent article that is generally perpendicular to the longitudinal direction.

Figure 1:
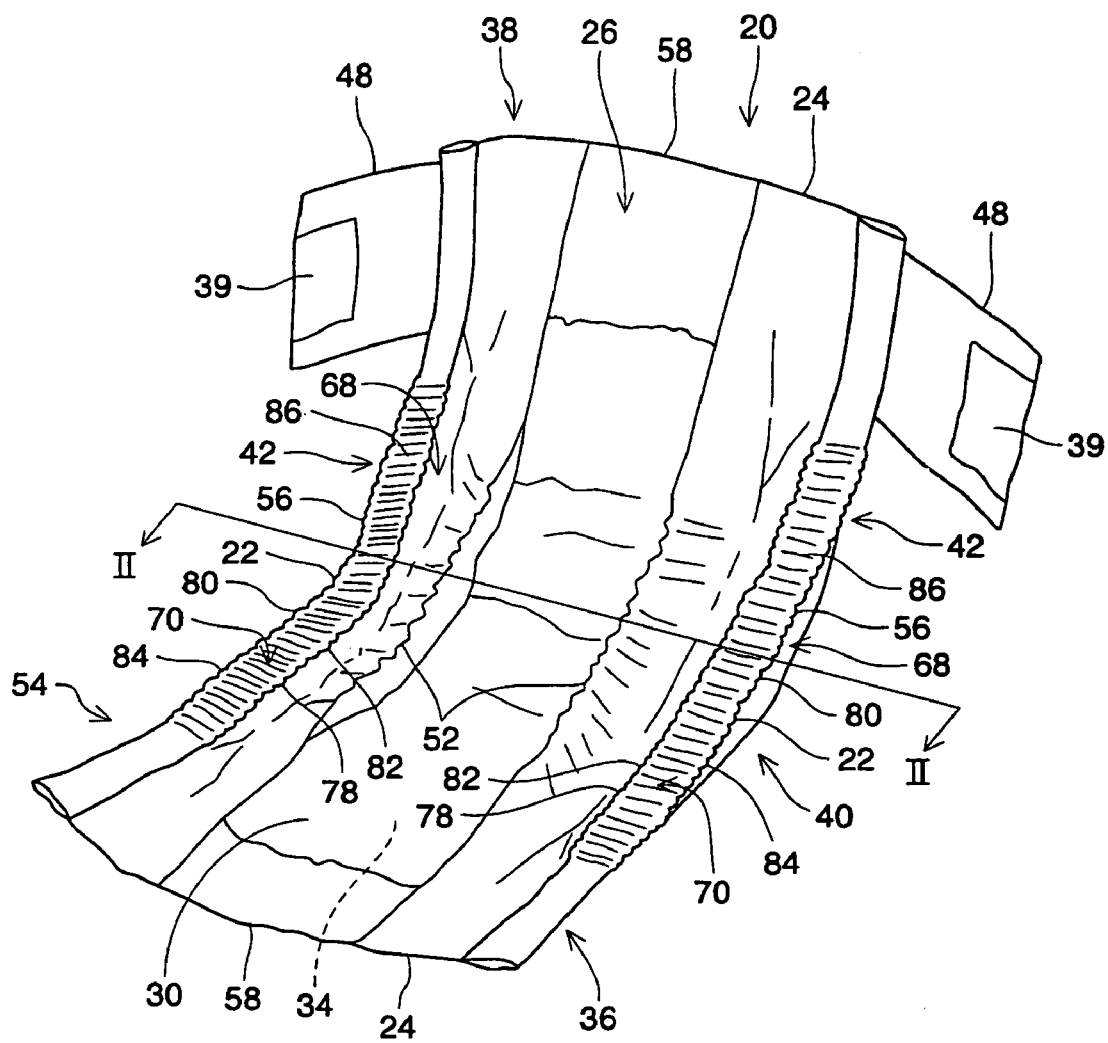
FIG. 1 is a perspective view of the diaper of one embodiment of the present invention.
Figure 2:
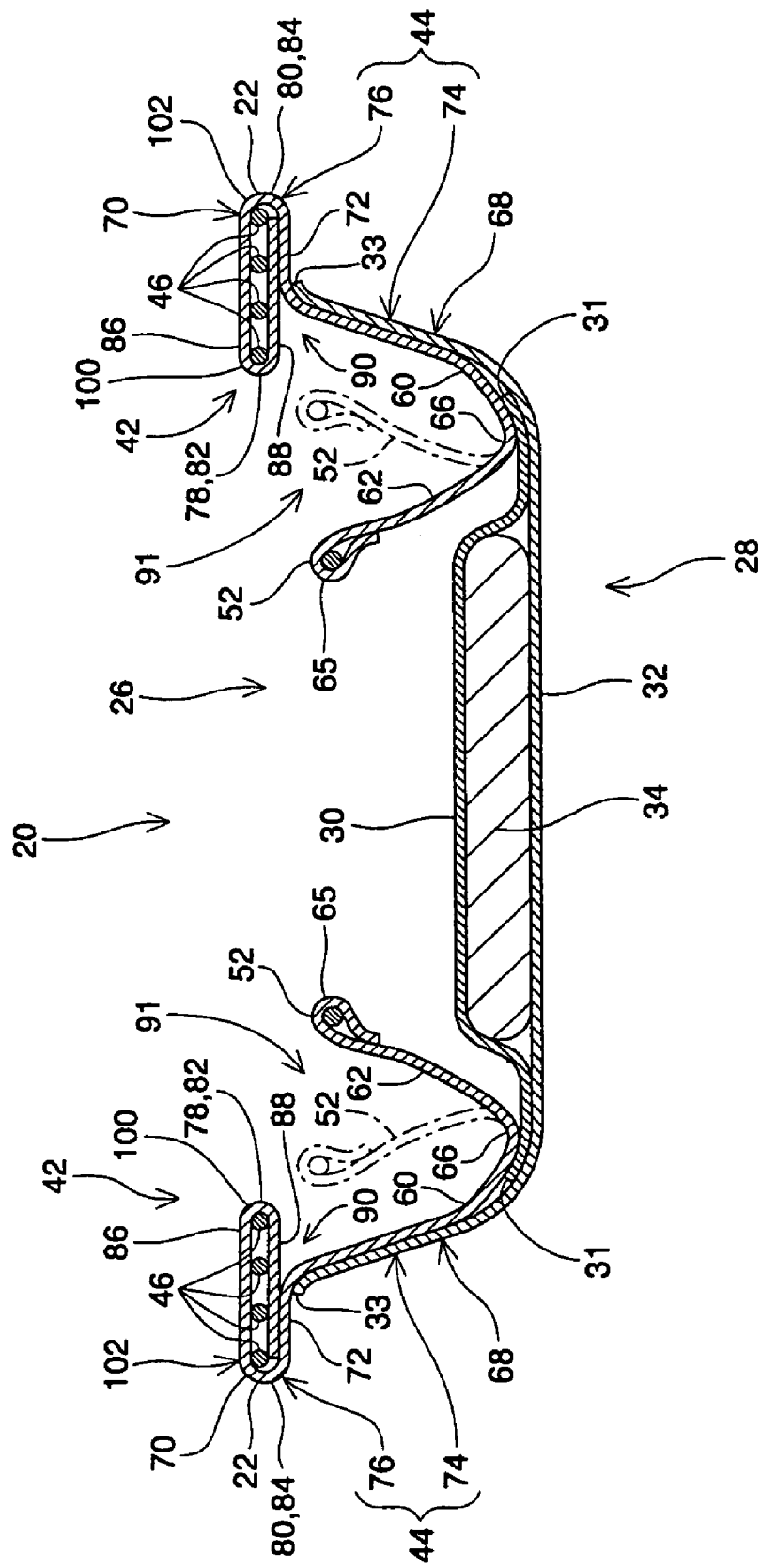
FIG. 2 is a cross-sectional view taken along the line II-II of FIG. 1.
Figure 3:
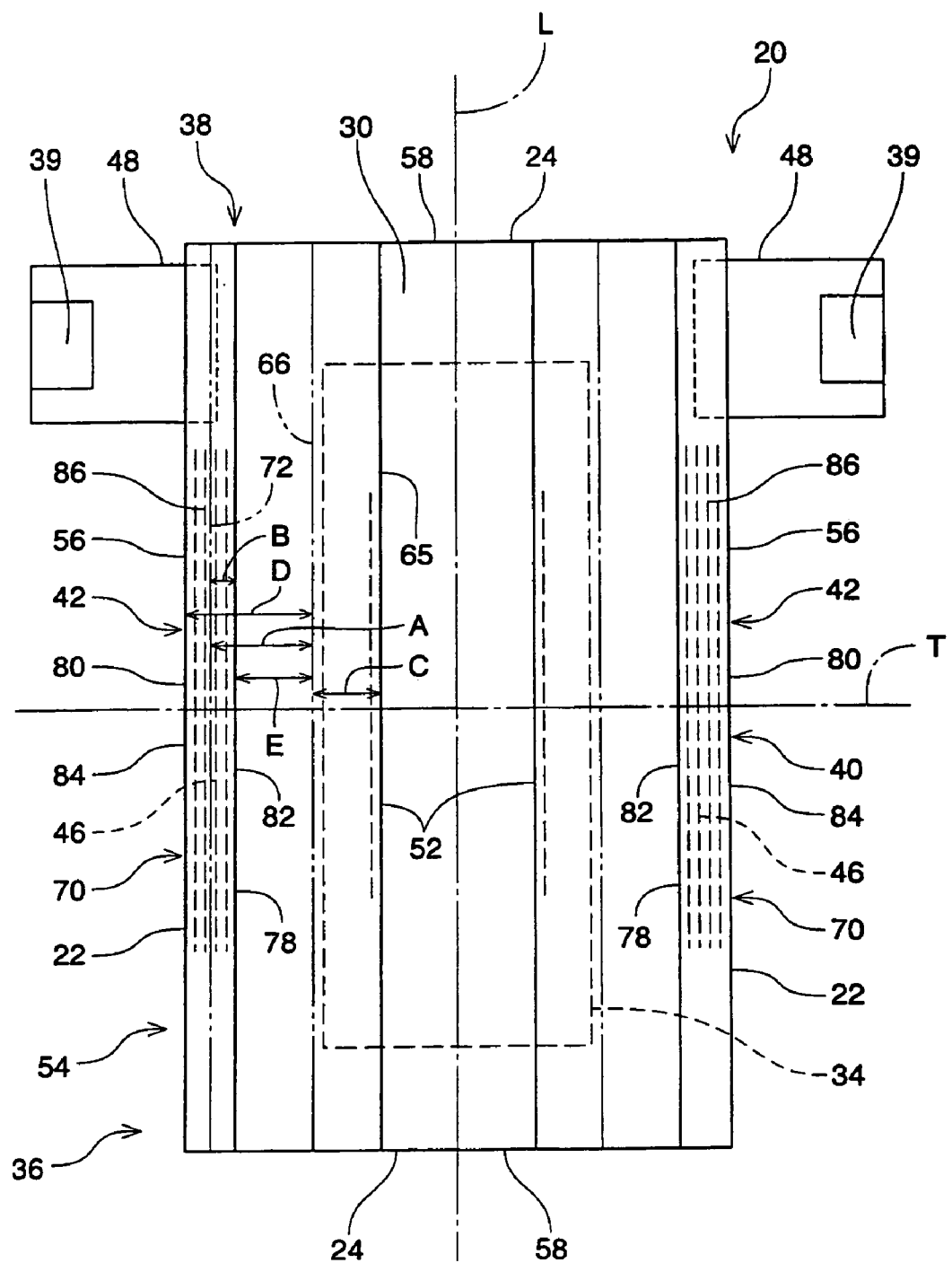
FIG. 3 is a top plan view of the diaper of FIG. 1 in its flat-out configuration.

FIG. 1 is a perspective view of the diaper 20 of one embodiment of the present invention. Referring to FIG. 2 showing a cross-sectional view taken along the line II-II of FIG. 1 and FIG. 3 showing a top plan view of the diaper 20 of FIG. 1 in its flat-out configuration as well, the diaper 20 has an inner surface 26 facing the wearer, an opposite outer surface 28, longitudinal centerline L, and lateral centerline T. The diaper 20 also has longitudinal side edges 22 running generally in the longitudinal direction of the diaper and lateral end edges 24 running between the longitudinal side edges 22 generally in the lateral direction of the diaper 20. The periphery of the diaper 20 is defined by the longitudinal side edges 22 and the lateral end edges 24. The diaper 20 further has a front waist region 36, a back waist region 38 and a crotch region 40 disposed between the front waist region 36 and the back waist region 38.

The diaper 20 comprises a chassis 54 and an ear panel 48 joined to the chassis 54. The chassis 54 has a generally rectangle shape in its flat-out configuration as shown in FIG. 3. The chassis 54 has lateral end edges 58 and longitudinal side edges 56. The lateral end edge 58 of the chassis 54 preferably defines the lateral end edge 24 of the diaper 20. The longitudinal side edges 56 of the chassis 54 preferably defines the longitudinal side edge 22 of the diaper 20 at least in the crotch region 40. The chassis 54 comprises a liquid pervious topsheet 30; a liquid impervious backsheet 32; an absorbent core 34, which is preferably positioned between at least a portion of the topsheet 30 and the backsheet 32; and a side flap 44 extending laterally outwardly from the absorbent core 34. The side flap 44 has a proximal flap 74 and a distal flap 76. The chassis 54 further comprises an elasticized outer leg cuff 42 disposed adjacent to the longitudinal side edge 22 in the crotch region 40. The elasticized outer leg cuff 42 has a base 68 and a gasket cuff 70 supported by the base 68 at a joint 72 of the base 68 to the gasket cuff 70. The gasket cuff 70 is provided with an elastic material 46 and has an inner cuff 100 extending laterally inwardly from the joint 72 and an outer cuff 102 extending laterally outwardly from the joint 72. The chassis 54 shown in FIG. 1 also may comprise barrier leg cuffs 52 and an elastic waist feature (not shown in Figures). The ear panel 48 is joined adjacent to the longitudinal side edge 56 of the chassis 54 and joined to an element constituting the chassis 54 such as a topsheet, a backsheet, an absorbent core, an elasticized outer leg cuff, a barrier leg cuff or combinations thereof by any known means such as adhesives or heat and pressure attachment such that the ear panel 48 extends laterally outwardly from the absorbent core 34. In the embodiment shown in FIG. 1, the ear panel 48 is joined to the backsheet 32 by heat and pressure attachment. A closure member such as a fastening tape 39 is provided to the longitudinal side edge of the ear panel 48.

The liquid pervious topsheet 30 is preferably positioned adjacent the body-facing surface of the absorbent core 34 and may be joined thereto and/or to the backsheet 32 by any attachment means known in the art. The topsheet 30 is preferably compliant, soft feeling, and non-irritating to the wearer's skin. Further, at least a portion of the topsheet 30 is liquid pervious, permitting liquid to readily penetrate through its thickness. A suitable topsheet 30 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Preferably, the topsheet 30 is made of a hydrophobic material or is treated to be hydrophobic in order to isolate the wearer's skin from liquids contained in the absorbent core 34. If the topsheet 30 is made of a hydrophobic material, preferably at least the upper surface of the topsheet 30 is treated to be hydrophilic so that liquids will transfer through the topsheet more rapidly.

The liquid impervious backsheet 32 is generally that portion of the diaper 20 positioned adjacent the garment-facing surface of the absorbent core 34. Backsheet 32 prevents the exudates absorbed and contained therein from soiling articles that may contact the diaper 20, such as bedsheets and undergarments. In preferred embodiments, the backsheet 32 is impervious to liquids (e.g., urine) and comprises a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the diaper 20 while still preventing exudates from passing through the backsheet 32. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097.

The absorbent core 34 may comprise any absorbent material that is generally compressible, conformable, non-irritating to the wearer's skin, and capable of absorbing and retaining liquids such as urine and other certain body exudates. The absorbent core 34 has longitudinal side edges and end edges and can be manufactured in a wide variety of sizes and shapes (e.g., rectangular, hourglass, "T"-shaped, asymmetric, etc.) and may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. In any case all or a portion of the core may include slits which allow the core to form openings when stretched into which fecal mater can flow. The configuration and construction of the absorbent core 34 may also be varied (e.g., the absorbent core(s) or other absorbent structure(s) may have varying caliper zones, a hydrophilic gradient, a superabsorbent gradient, or lower average density and lower average basis weight acquisition zones; or may comprise one or more layers or structures). However, the total absorbent capacity of the absorbent core 34 should be compatible with the design loading and the intended use of the diaper 20.

The barrier leg cuff 52 has a proximal edge 66 and a distal edge 65. The barrier leg cuff 52 is joined adjacent the longitudinal side edges 56 of the chassis 54. In the embodiment shown in FIG. 2, the barrier leg cuff 52 is joined onto the topsheet 30 at the proximal edge 66 of the barrier leg cuff 52 by any known means. Alternatively, the barrier leg cuff 52 may be joined to the backsheet 32 without being joined to the topsheet 30. The barrier leg cuff 52 may comprise any known materials such as a nonwoven material which may be liquid impervious and/or hydrophobic. The barrier leg cuff 52 has a lateral inner portion 62 extending laterally inwardly from the proximal edge 66 and being provided with an elastic materials at the distal edge 65 of the lateral inner portion 62 to space the lateral inner portion 62 upwardly away from the topsheet 30 to serve as a barrier to leakage of body exudates. The barrier leg cuff 52 also has a lateral outer portion 60 extending laterally outwardly from the proximal edge 66 and being joined onto the lateral extension of the topsheet 30 and the lateral extension of the backsheet 32 in the embodiment shown in FIG. 2. The lateral outer portion 60 shown in FIG. 2 extends further laterally outwardly beyond both the longitudinal side edge 31 of the topsheet 30 and the longitudinal side edge 33 of the backsheet 34.

The side flap 44 shown in FIGS. 1, 2 and 3 is disposed adjacent the longitudinal side edge 56 of the chassis 54 so as to extend laterally outwardly from the absorbent core 34 in the embodiment shown in FIG. 2. The side flap 44 is preferably formed with a material which is liquid impervious and/or hydrophobic. The side flap 44 has a proximal flap 74 which is laterally proximate to the absorbent core 34 and a distal flap 76 which extends laterally outwardly from the proximal flap 74. The proximal flap 74 and the distal flap 76 may be formed by an integral material or alternatively may be formed by separate materials joined to each other. The side flap 44 may be formed by a single layer of material, or two or more layers of material. In the embodiment shown in FIG. 2, a portion of the proximal flap 74 proximate to the proximal edge 66 is formed by the lateral extension of the topsheet 30, the lateral extension of the backsheet 32 and the lateral outer portion 60. A portion of the proximal flap 74 laterally outside thereof is formed by the lateral extension of the backsheet 32 and the lateral outer portion 60 of the barrier leg cuff 52. This configuration allows the proximal flap 74 to be liquid impervious because the liquid impervious backsheet 32 extends into the proximal flap 74. In the embodiment, the distal flap 76 is formed by only the lateral outer portion 60 of the barrier leg cuff 52. It is preferable that a portion of the side flap comprising two or more layers are joined throughout the coextensive area of the layers by any known means such as adhesives. This allows the longitudinal side edge 33 of the backsheet 34 not to separate from the lateral outer portion 60 of the barrier leg cuff 52 and contributes to provide a tailored outer edge of the diaper.

Many variations for forming the side flap are possible. In the embodiment shown in FIG. 2, the proximal flap 74 may be formed only by the lateral outer portion 60 of the barrier leg cuff 52 without the lateral extension of the backsheet 32. When the barrier leg cuff 52 is formed by a hydrophobic and/or liquid impervious material, the proximal flap 74 may have a sufficient liquid impermeability even though there is no backsheet 32 extended thereinto. This design also allows the proximal flap 74 to be highly breathable and less bulky. In the embodiment shown in FIG. 2, the topsheet 30 may extend into the proximal flap 74 such that the topsheet 30 extends to the same extent as the backsheet 32.

Figure 4:
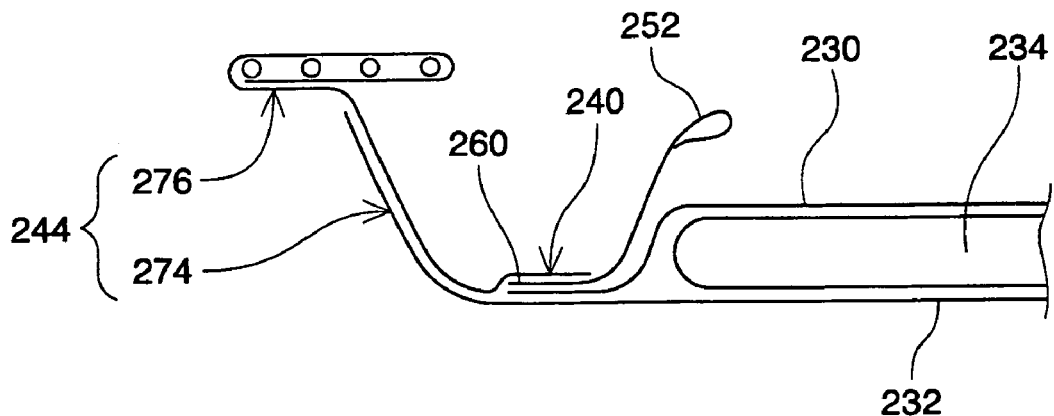
FIG. 4 is a first alternative embodiment of the side flap.
Figure 5:
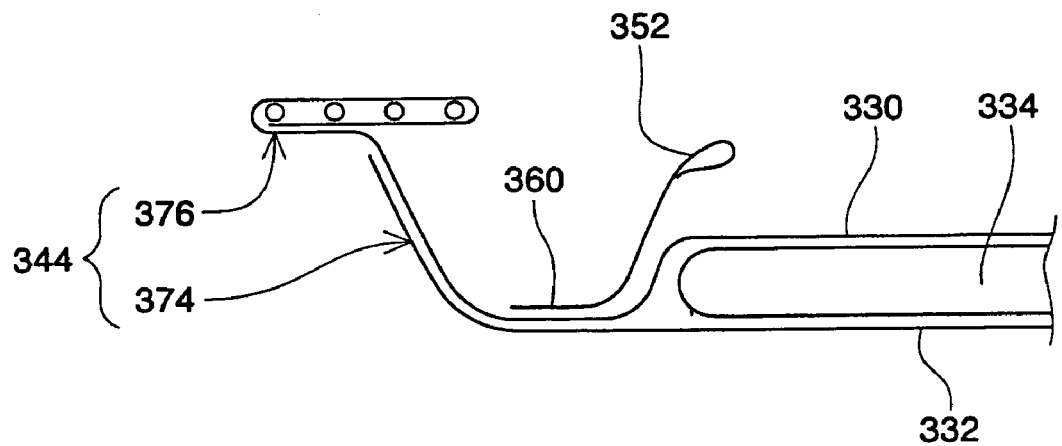
FIG. 5 is a second alternative embodiment of the side flap.
Figure 6:
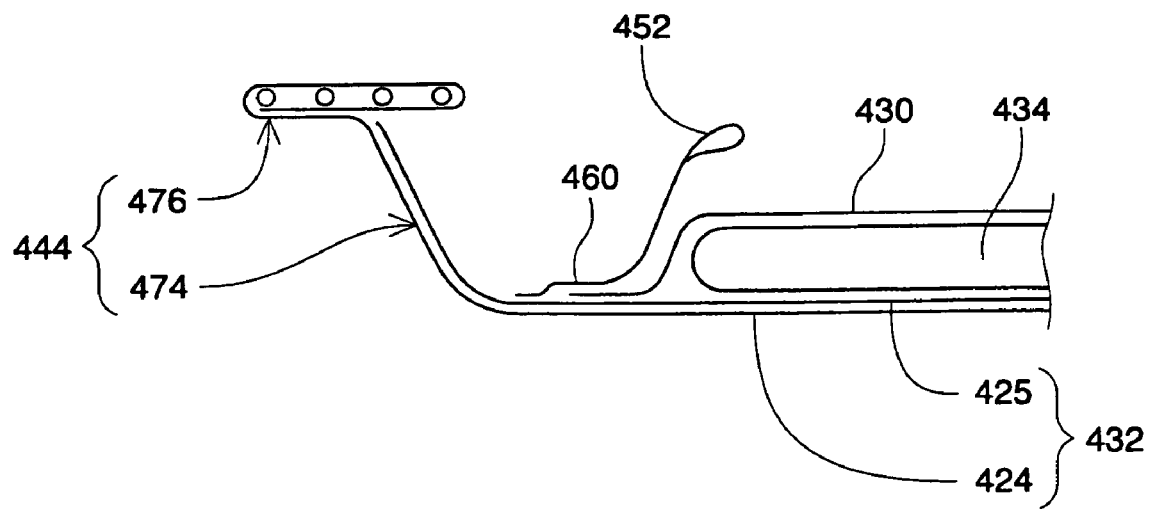
FIG. 6 is a third alternative embodiment of the side flap.
Figure 7:
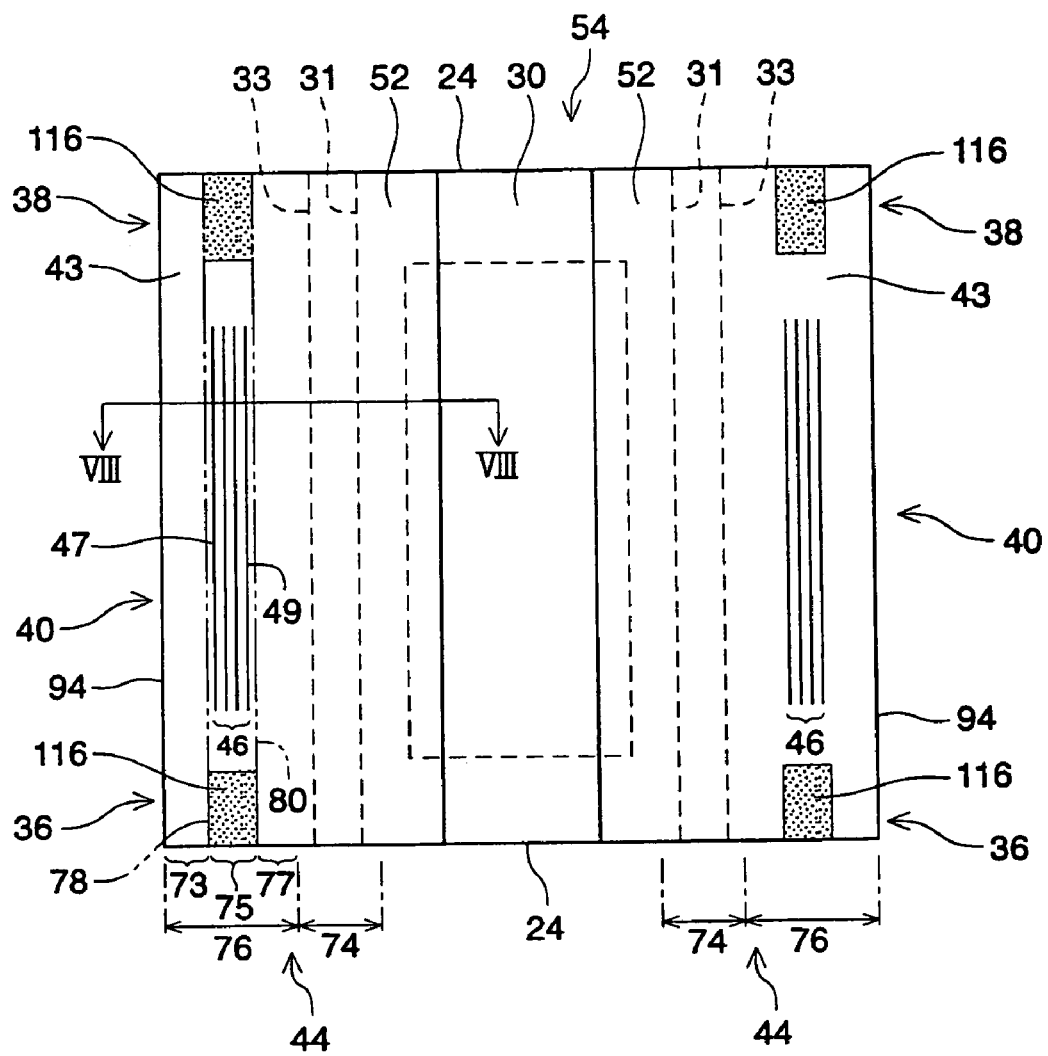
FIG. 7 is a top plan view showing the first step of forming the elasticized outer leg cuff.
Figure 8:
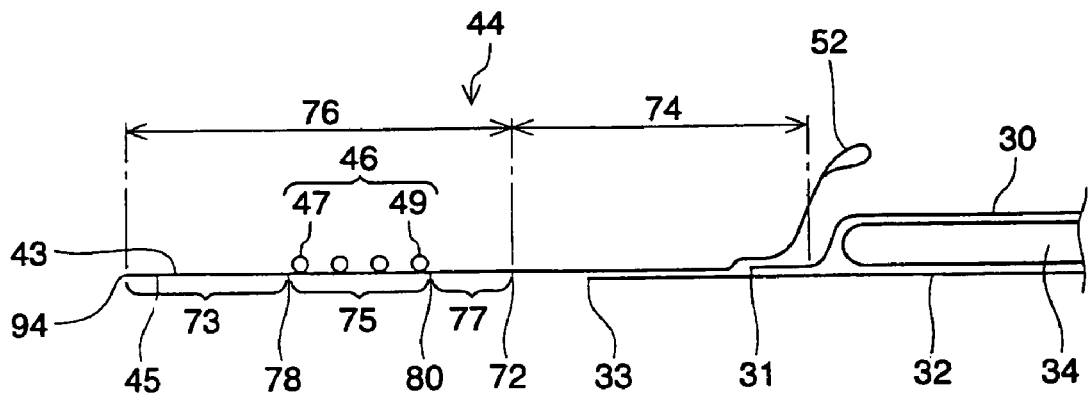
FIG. 8 is a cross-sectional view taken along the line VIII-VIII of FIG. 7.

Shown in FIGS. 4, 5, and 6 are an alternative embodiment of the side flap 44. In the embodiment shown in FIG. 4, the barrier leg cuff 252 terminates in the proximal flap 274 without extending into the distal flap 276. A side flap sheet 240 is provided to form the side flap 244 together with the lateral extension of the backsheet 232. A portion of the proximal flap 274 proximate to the absorbent core 234 is formed by the lateral outer portion 260 of the barrier leg cuff 252, the lateral extension of the topsheet 230, the lateral extension of the backsheet 232 and the side flap sheet 240. A portion of the proximal flap 274 outside thereof is formed by the lateral extension of the backsheet 232 and the side flap sheet 240. In the embodiment, the distal flap 276 is formed by only the side flap sheet 240. At least a portion of the side flap sheet 240 forming the distal flap 276 or the entirety of the side flap sheet 240 is preferably hydrophobic and/or liquid impervious. In the embodiment shown in FIG. 5, the lateral extension of the topsheet 330 extends into the proximal flap 374 and the distal flap 376 to form the side flap 344. A portion of the proximal flap 374 proximate to the absorbent core 334 is formed by the lateral extension of the topsheet 330, the lateral extension of the backsheet 332 and the lateral outer portion 360 of the barrier leg cuff 352. A portion of the proximal flap 374 outside thereof is formed by the lateral extension of the backsheet 332 and the lateral extension of the topsheet 330. In the embodiment, the distal flap 376 is formed by only the lateral extension of the topsheet 330. At least a portion of the topsheet 330 forming the distal flap 376 is preferably rendered to be hydrophobic and/or liquid impervious. In the embodiment shown in FIG. 6, the backsheet 432 comprises an outer nonwoven 424 covering the liquid impervious backsheet film 425. The outer nonwoven 424 extends into the proximal flap 474 and the distal flap 476 to form the side flap 444. A portion of the proximal flap 474 proximate to the absorbent core 434 is formed by the lateral extension of the topsheet 430, the lateral extension of the backsheet film 425, the lateral outer portion 460 of the barrier leg cuff 452 and the outer nonwoven 424. A portion of the proximal flap 474 outside thereof is formed by the lateral extension of the backsheet 432 and the outer nonwoven 424. In the embodiment, the distal flap 476 is formed by only the outer nonwoven 424. At least a portion of the outer nonwoven 424 forming the distal flap 476 or the entirety of the outer nonwoven 424 is preferably rendered to be hydrophobic and/or liquid impervious.

Further alternative embodiments of the side flap are possible. For example, the side flap may comprise any other material joined to the chassis 54 or may comprise any combination of an extension of the topsheet, an extension of the backsheet, an extension of a barrier leg cuff, and/or any other material. While the distal flap shown in FIGS. 4, 5 and 6 is formed with only one layer of the material extending into the distal flap, it may comprise two or more layers extending into the distal flap. As explained hereinbelow, the distal flap is used to form the elasticized outer leg cuff, a portion of which touches the skin of the wearer. Therefore, it is preferable that the surface of the distal flap which will touch the skin of the wearer comprises resilient, flexible and soft material such as a nonwoven or woven.

The elasticized outer leg cuff 42 shown in FIGS. 1, 2 and 3 comprises the side flap 44 and the elastic material 46. The outer leg cuff 42 is a generally T-shaped cuff having a base 68 and a gasket cuff 70 supported by the base 68 at a joint 72 of the base to the gasket cuff 70. The term "generally T-shaped" means that the base branches from the gasket cuff at the joint between the inner cuff and the outer cuff of the gasket cuff such that the base forms an angle with the inner cuff and an angle with an outer cuff in a cross-sectional view when the diaper is in a relaxed configuration. Therefore, the base may form an angle of 90 degree or an angle other than 90 degree with the inner cuff and the outer cuff. The base 68 comprises the proximal flap 74 and extends between the longitudinal side edge of the absorbent core 34 and the joint 72. The gasket cuff 70 comprises the distal flap 76 and disposed on the top of the base 68.

The gasket cuff 70 has an inner cuff 100 extending laterally inwardly from the joint 72 and an outer cuff 102 extending laterally outwardly from the joint 72 as shown in FIG. 2. The gasket cuff 70 is formed with the distal flap 76 of the side flap 44 being folded at least twice along a first folding line 78 and a second folding line 80 laterally inwardly toward the longitudinal centerline L of the diaper 20 and is formed into a thin flat sleeve-like shape in a cross-section having an inner longitudinal edge 82, an outer longitudinal edge 84, a top gasket cuff surface 86 and an opposite surface 88. The top gasket cuff surface 86 has a generally flat surface in cross-section as shown in FIG. 2 while it may have a degree of undulation in the longitudinal direction formed by the gather caused by the elastic material 46 as shown in FIG. 1. The gasket cuff 70 may be formed into a different cross-section such as circle, oval, U-shape, or V-shape while the thin flat shape is preferable. In the embodiment shown in Figures, the first folding line 78 and the second folding line 80 correspond to the inner longitudinal edge 82 and the outer longitudinal edge 84 of the gasket cuff 70, respectively. The opposite surface 88 of the gasket cuff 70 is joined with the base 68 at the joint 72 which is located between the inner cuff 100 and the outer cuff 102 by any known means such as adhesives, preferably at the middle between the inner cuff 100 and the outer cuff 102. The gasket cuff 70 is provided with the elastic material 46 such as a plurality of elastic strands, a single elastic belt or the like. The elastic material 46 is encased into the thin sleeve-like space of the gasket cuff 70 and joined to the inner surface thereof. In the embodiment shown in FIG. 2, the elastic material 46 includes four elastic strands. Two elastic strands are disposed along the inner and outer longitudinal edges 82 and 84 and the other two elastic strands are disposed adjacent to the joint 72, preferably on the laterally opposite sides of the joint 72. Alternatively, the elastic strands 46 may comprise two or more elastic strands or may comprise a single elastic belt having a width extending between the inner and outer longitudinal edges 82 and 84. The elastic material 46 extends generally in the crotch region 40 such that the elastic material 46 provides elasticity for the gasket cuff 70 and provides a gather to the gasket cuff 70 when the diaper 20 is relaxed as shown in FIG. 1. The elastic material 46 also provides a force to stand the base 68 generally upwardly from the absorbent core 34 as shown in FIG. 2. Thus, the combination of the base 68 and the gasket cuff 70 provides a generally T-shaped cuff when the outer leg cuff 42 is in a relaxed configuration. It also provides a channel 90 between the opposite surface 88 of the inner cuff 100 and the inner surface of the base 68 to enhance containment properties of body exudates. The inner cuff 100 works as an effective barrier to prevent body exudates to overflow the gasket cuff 70.

Each of the elastic materials may have different contraction force. The elastic material disposed adjacent the inner longitudinal edge 82 may have higher contraction force than the elastic material disposed adjacent the outer longitudinal edge 84 so that the inner cuff 100 is upwardly spaced away from the base 68 to provide more space between the inner cuff 100 and the base 68. Alternatively, the elastic material disposed adjacent the outer longitudinal edge 84 may have higher contraction force than the elastic material disposed adjacent the inner longitudinal edge 82 so that the inner cuff 100 is downwardly biased toward the base 68 to reduce the space between the inner cuff 100 and the base 68. The contraction force of the elastic materials disposed adjacent the inner longitudinal edge 82 and the outer longitudinal edge 84 may be different from that of the elastic materials disposed adjacent the joint 72. In such a case, it is preferable that the elastic material disposed adjacent the joint 72 has higher contraction force than the elastic materials disposed adjacent the inner longitudinal edge 82 and the outer longitudinal edge 84. Alternatively, the elastic material disposed adjacent the joint 72 may have lower contraction force than the elastic materials disposed adjacent the inner longitudinal edge 82 and the outer longitudinal edge 84.

The gasket cuff 70 preferably has a lateral width to provide a good sealing effect against the leakage of body exudates when the gasket cuff 70 touches the skin of the wearer in use. The wide gasket cuff 70 efficiently provides a wide skin contact area for a good sealing effect. However, such a wide gasket cuff may cause uncomfortableness to the wearer because of the wide skin contact area. Therefore, the gasket cuff 70 may have the lateral width of between about 3 mm and about 50 mm, preferably between about 5 mm and about 30 mm, more preferably about 10 mm and about 20 mm along the lateral centerline T at the crotch region 40 of the diaper 20. The lateral width can be measured as the width between the inner longitudinal edge 82 and the outer longitudinal edge 84 of the gasket cuff 70. The gasket cuff 70 may have the same lateral width throughout its longitudinal length. However, the lateral width of the gasket cuff 70 may vary along the longitudinal length of the gasket cuff 70. For example, the gasket cuff 70 may have the lateral width at the crotch region 40 greater than at the front and/or back waist region 36, 38.

The base 68 preferably has a lateral width to provide a good containment characteristics when the base 68 stands upwardly from the absorbent core 34 as shown in FIG. 2. The base 68 may have the lateral width of between about 10 mm and about 100 mm, preferably between about 20 mm and about 80 mm, more preferably about 30 mm and about 70 mm along the lateral centerline T at the crotch region 40 of the diaper 20. The lateral width can be measured as the width between the joint 72 and the longitudinal side edge of the absorbent core 34. The base 68 may have the same lateral width throughout its longitudinal length. However, the lateral width of the base 68 may vary along the longitudinal length of the base 68. For example, the base 68 may have the lateral width at the crotch region 49 greater than at the front and/or back waist region 36, 38.

It is desirable to dispose the barrier leg cuff 52 and the elasticized outer leg cuff 42 in a specific relationship. The proximal edge 66 of the barrier leg cuff is positioned on the base 68 of elasticized outer leg cuff 42 such that the barrier leg cuff 52 is disposed inboard of the gasket cuff 70 to form a pocket 91 by combination of the inner cuff 100 of the gasket cuff 70, the base 68 and the barrier leg cuff 52. The pocket 90 provides space to contain body exudates overflowed the barrier leg cuff 52. As the barrier leg cuff 52 is positioned inboard of the gasket cuff 70, the barrier leg cuff 52 serves a primary leakage prevention and the gasket cuff 70 serves a secondary leakage prevention. The barrier leg cuff 52 also prevents the inner cuff 100 from being exposed to body exudates contained in the space between a pair of barrier leg cuffs 52. Therefore, leakage prevention effect of the inner cuff 100 will not be deteriorated by body exudates and maintained over long period of wearing time just in case body exudates overflows the barrier leg cuff 52.

As shown in FIG. 3, it is preferable that the distance A between the joint 72 and the proximal edge 66 of the barrier leg cuff 52 is greater than the distance B between the joint 72 and the inner longitudinal edge 82 of the inner cuff 100 in the crotch region 40 of the diaper 20. If this is not satisfied, the lateral inner portion 62 of the barrier leg cuff 52 may touch the inner longitudinal edge 82 of the inner cuff 100 and a pocket 91 may not be formed when the diaper is used. The distance A may be between about 5 mm and about 60 mm, preferably between about 8 mm and about 50 mm, more preferably between about 10 mm and about 40 mm. The distance B may be between about 1.5 mm and about 25 mm, preferably between about 2.5 mm and about 15 mm, more preferably between about 5 mm and about 10 mm. It is also preferable that the distance C between the distal edge 65 and the proximal edge 66 of the barrier leg cuff 52 is less than the distance D between the proximal edge 66 and the outer longitudinal edge 84 of the outer cuff 102 in the crotch region 40 of the diaper 20. If this is not satisfied, the distal edge 65 may be positioned laterally outwardly beyond the outer longitudinal edge 84 of the outer cuff 102 when the barrier leg cuff 52 is accidentally flipped over laterally outwardly. This hinders the gasket cuff 70 from serving the secondary leakage prevention. The distance C may be between about 10 mm and about 80 mm, preferably between about 15 mm and about 65 mm, more preferably between about 20 mm and about 50 mm. The distance D may be determined by summing the distance A and the distance B. It is more preferable that the distance A between the joint 72 and the proximal edge 66 is greater than the distance C between the distal edge 65 and the proximal edge 66 in the crotch region 40 of the diaper 20. It is even more preferable that the distance C between the distal edge 65 and the proximal edge 66 is less than the distance E between the proximal edge 66 and the inner longitudinal edge 82 of the inner cuff 100 in the crotch region 40 of the diaper 20. When this is satisfied, it allows to reduce the risk that the distal edge 65 of the barrier leg cuff 52 touches the inner cuff 100 even when the barrier leg cuff 52 is accidentally flipped over laterally outwardly as shown by an imaginary line in FIG. 2. Therefore, a pocket 91 can be effectively formed. The distances are measured in a stretched flat-out condition of the diaper 20 as shown in FIG. 3. The distance E may be determined by the difference of the distance A minus the distance B.

FIGS. 7 to 12 show a process to form the elasticized outer leg cuff 42 of FIGS. 1, 2 and 3 from the side flap 44 and the elastic material 46. In the embodiment shown in FIGS. 7 and 8, the side flap 44 is preassembled by joining the topsheet 30, the backsheet 32 and the barrier leg cuff 52 prior to forming the outer leg cuff 42. The side flap 44 has the proximal flap 74 and the distal flap 76 which is virtually separated by the point of the joint 72 in the embodiment shown in FIG. 8. The side flap 44 has a first surface 43 and a second surface 45. The distal flap 76 has a first flap portion (first folded portion) 73, a second flap portion (second folded portion) 75 and a third flap portion 77. The first flap portion 73 and the second flap portion 75 are divided by a first folding line 78 shown by an imaginary line in FIG. 7. The second flap portion 75 and the third flap portion 77 are divided by a second folding line 80 shown by an imaginary line in FIG. 7. In the embodiment shown in FIGS. 7 and 8, the elastic materials 46 comprising four elastic strands are stretched and disposed on the first surface 43 of the second flap portion 75 of the distal flap 76. The elastic strands 46 are then joined thereto by any known means such as adhesives. The elastic strands 46 extend in the region between the first folding line 78 and the second folding line 80 in the crotch region 40. The elastic strands 46 may extend into the front waist region 36 and/or the back waist region 38. The first flap portion 73 has a lateral width to cover four of the elastic strands 46 when the first flap portion 73 is folded as explained hereinbelow and has the almost same lateral width as the second flap portion 75. The third flap portion 77 is almost half of the lateral width of the second flap portion 75. First cuff forming adhesives 116 are provided to join the first flap portion 73 to the second flap portion 75 adjacent to the lateral end edge 24 when the first flap portion 73 is folded onto the second flap portion 75.

Figure 9:
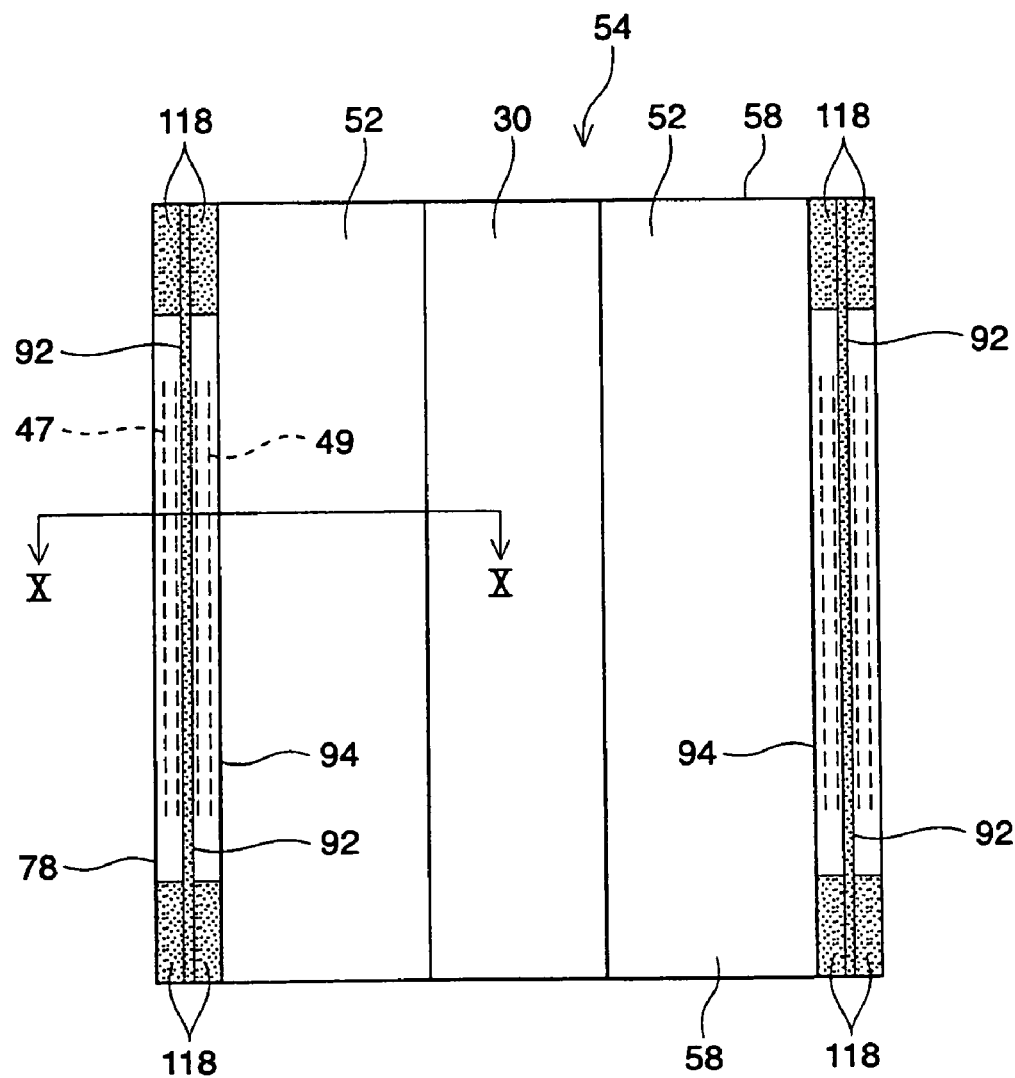
FIG. 9 is a top plan view showing the second step of forming the elasticized outer leg cuff.
Figure 10:
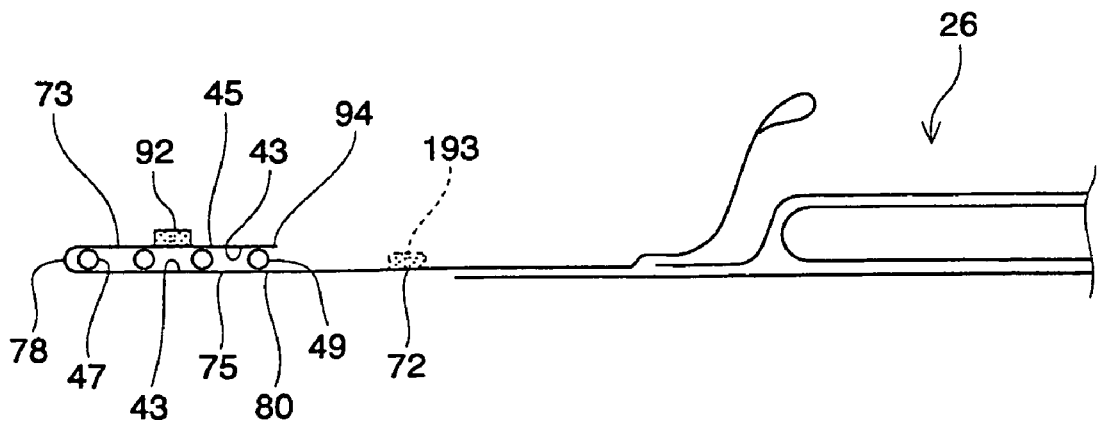
FIG. 10 is a cross-sectional view taken along the line X-X of FIG. 9.

The distal flap 76 of the side flap 44 is then folded once along the first folding line 78 adjacent the outermost elastic strands 47 laterally inwardly toward the longitudinal centerline L of the diaper 20 as shown in FIGS. 9 and 10. The first flap portion 73 of the distal flap 76 is folded toward the side of the inner surface 26 of the diaper 20. The distal flap 76 sandwiches the four of elastic strands 46 between the first folded portion (first flap portion) 73 and the second flap portion 75. When the elastic strands 46 are sandwiched, the elastic strands 46 are preferably joined to the first surface 43 of the first folded portion 73 and the second flap portion 75. A joint adhesive 92 is provided on the second surface 45 of the first folded portion 73 to form the joint 72 between the gasket cuff 70 and the base 68. The joint adhesive 92 is disposed as a continuous straight line between the first folding line 78 and the second folding line 80 in the configuration in which the gasket cuff 70 is assembled as shown in FIG. 2, preferably at the middle therebetween such that the gasket cuff 70 and the base 68 form a generally T-shaped cuff. In other words, the joint adhesive 92 is provided at the middle between the first folding line 78 and the longitudinal side edge 94 of the distal flap 76. In the embodiment shown in FIG. 9, the joint adhesive 92 extends continuously in the longitudinal direction between the lateral end edges 58 of the chassis 54. As far as the gasket cuff 70 and the base 68 form a generally T-shaped cuff, the joint adhesive may take any shape such as a wavy line, or a dotted line, or any position. While the joint adhesive 92 is provided only at the middle between the first folding line 78 and the longitudinal side edge 94 of the distal flap 76 in the embodiment shown in FIGS. 9 and 10, the joint adhesive 92 may be provided between the position of the joint adhesive 92 shown in FIGS. 9 and 10 and the longitudinal side edge 94 of the distal flap 76. The joint adhesive 92 may be provided on the first folded portion 73 before or after the distal flap 76 is folded into a configuration shown in FIGS. 9 and 10. Alternatively, the joint adhesive 92 may be provided on the position of the side flap 44 corresponding to the joint 72 as shown by a reference number 193 in FIG. 10. Second cuff forming adhesives 118 are provided to join the first flap portion 73 to the third flap portion 77 and a portion inside thereof adjacent to the lateral end edge 24 when the first flap portion 73 is joined onto third flap portion 77 and a portion inside thereof.

Figure 11:
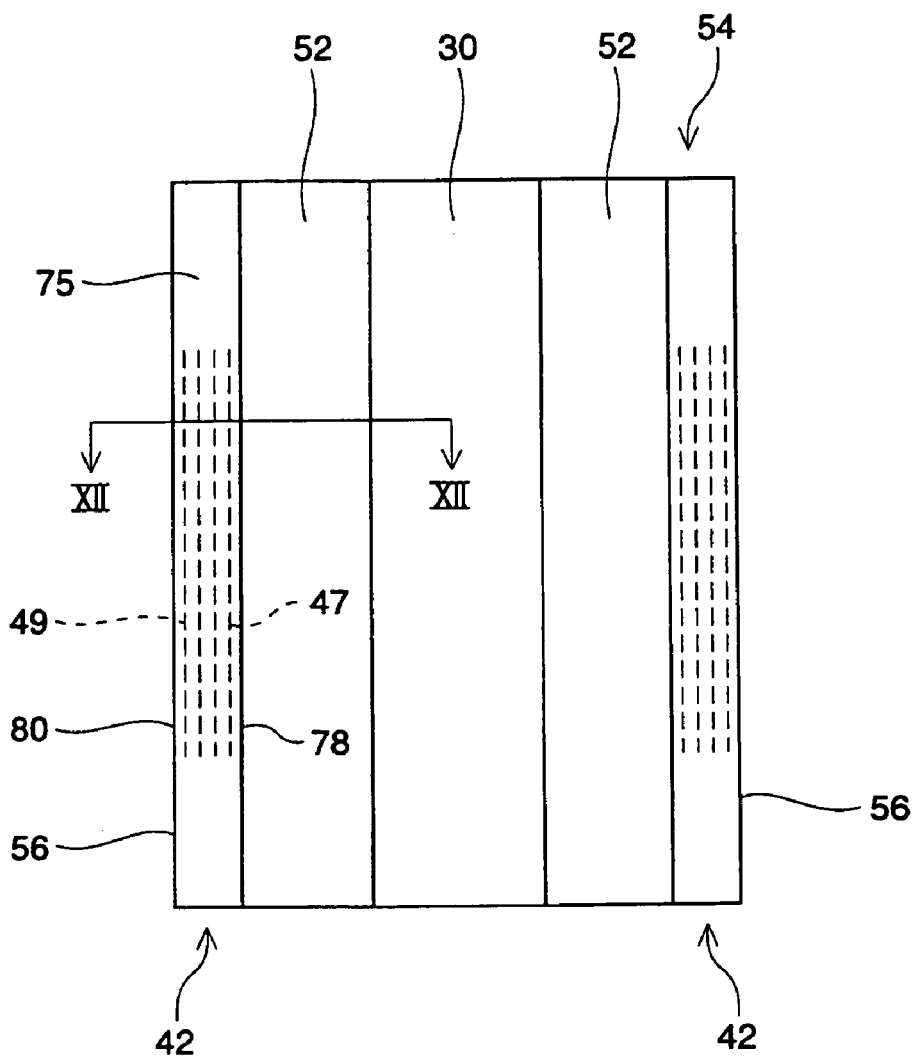
FIG. 11 is a top plan view showing the third step of forming the elasticized outer leg cuff.
Figure 12:
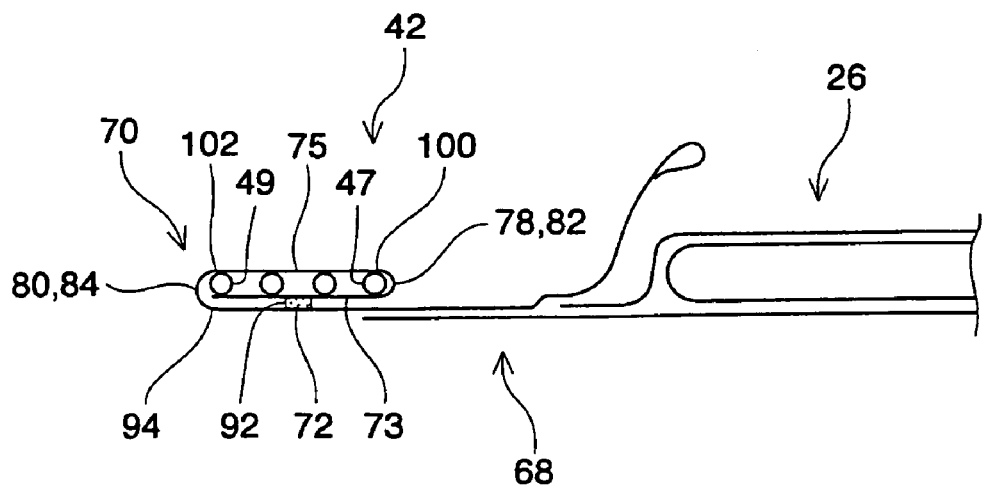
FIG. 12 is a cross-sectional view taken along the line XII-XII of FIG. 11.

The distal flap 76 having the four elastic strands 46 sandwiched by the first flap portion 73 and the second flap portion 75 is then again folded along the second folding line 80 adjacent the innermost elastic strands 49 laterally inwardly toward the longitudinal centerline L of the diaper 20 as shown in FIGS. 11 and 12. The distal flap 76 is folded toward the side of the inner surface 26 of the diaper 20. The distal flap 76 encases the four of elastic strands 46 by the first folded portion 73, the second folded 75, the first folding line 78 and the second folding line 80. The first folding line 78 and the second folding line 80 correspond to the inner longitudinal edge 82 and the outer longitudinal edge 84 of the gasket cuff 70, respectively. In the embodiment shown in FIG. 12, the first folded portion 73 has a lateral width such that the longitudinal side edge 94 of the distal flap 76 is hidden inside the gasket cuff 70. The joint adhesive 92 forms the joint 72 between the gasket cuff 70 and the base 68, whereby the inner cuff 100 and the outer cuff 102 are formed. In addition, it forms the gasket cuff 70 and the base 68 which constitute the outer leg cuff 42. The outer leg cuff 42 is provided along the longitudinal side edge 56 of the chassis 54. The outer longitudinal edge 84 of the gasket cuff 70 defines the longitudinal side edge 56 of the chassis 54. When the outer leg cuff 42 is in a relaxed configuration, the outer leg cuff 42 has a generally T-shaped configuration having a thin flat shaped gasket cuff 70 and the generally upwardly standing base 68.

The elasticized outer leg cuff 42 thus formed has several benefits. The gasket cuff 70 of the outer leg cuff 42 formed into a thin flat sleeve-like shape and having a flat top gasket cuff surface 86 provides an effective gasket seal between the wearer's skin and the surface 86. The gasket cuff 70 is provided with a degree of stiffness by being folded at least twice while it is still gentle and soft to the skin of the wearer. Therefore, the sealing effect between the wearer's skin and the surface 86 is enhanced. In addition, the gasket cuff 70 having a degree of stiffness prevents or at least reduce the outer longitudinal edge 84 of the gasket cuff 70 to be flipped over laterally inwardly toward the longitudinal centerline L of the diaper 20. Therefore, the user or wearer does not have to pay much attention to make sure whether or not the gasket cuff is flipped over when the wearer wears the diaper 20 and/or whether the gasket cuff 70 properly fits the wearer. The gasket cuff 70 of the present invention has the outer longitudinal edge 84 and the inner longitudinal edge 82 formed by folding the distal flap 76 at least twice laterally inwardly toward the longitudinal centerline L of the diaper 20. Not only this provides a cost effective and simple operation for forming the gasket cuff 70, but also it provides the gasket cuff 70 with a tailored appearance compared to the conventional outer leg cuff having exposed outer edges formed with cut or trimmed side edges which give a poor appearance. When the gasket cuff 70 comprises a nonwoven material, it also provides a soft and cloth like appearance to the gasket cuff.

Figure 13:
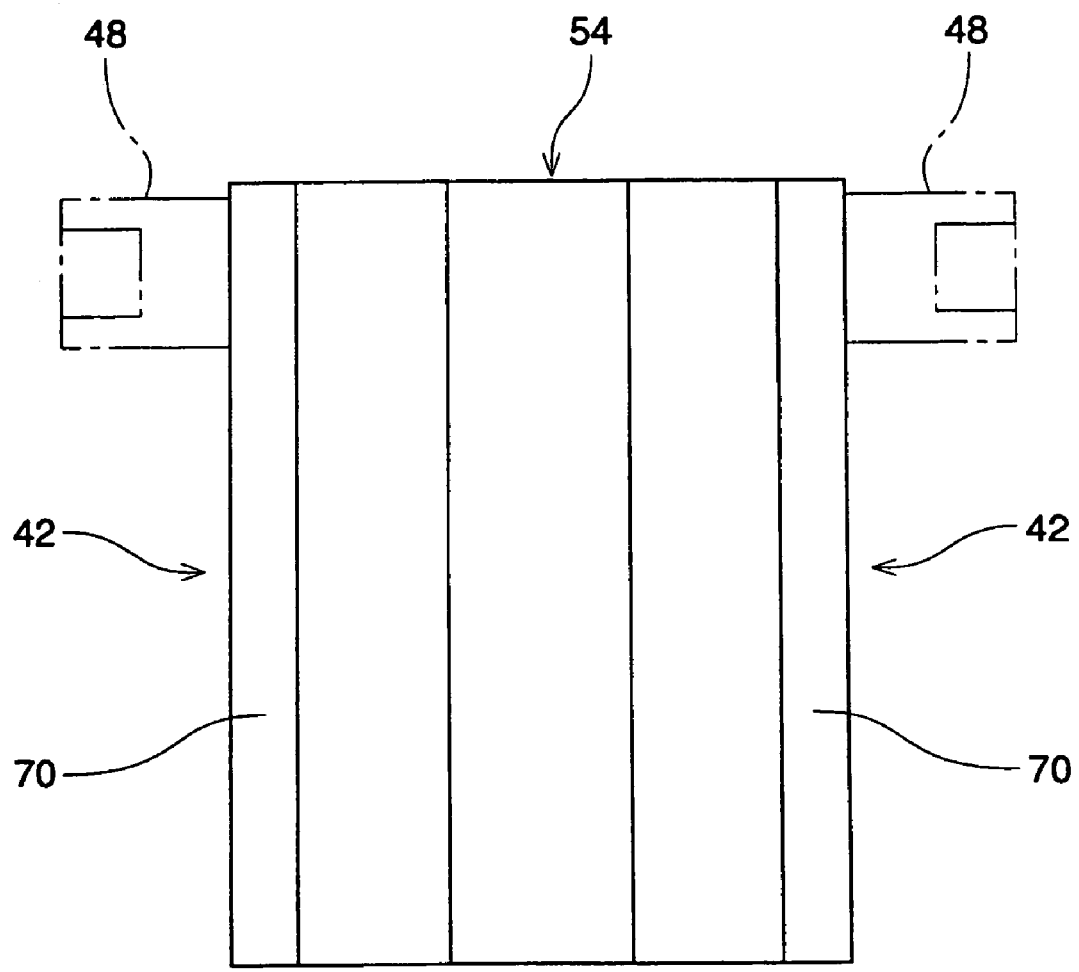
FIG. 13 is a top plan view of the diaper having the ear panel in its flat-out configuration.

The ear panel 48 is provided adjacent the longitudinal side edge 56 of the chassis 54 to extend laterally outwardly from the absorbent core 34. The ear panel 48 may be joined to the chassis 54 before the gasket cuff 70 of the outer leg cuff 42 is formed by folding the distal flap 76 of the side flap 44. However, when the ear panel 48 is joined to the chassis 54 prior to forming the outer leg cuff 42, the folding operation of the distal flap 76 requires a complicated operation to make sure that the folding operation of the distal flap 76 does not fold the ear panel 48 together with the distal flap 76. Therefore, it is preferable that the ear panel 48 is joined to the chassis 54 after the outer leg cuff 42 is formed. In other words, the gasket cuff 70 is preferably formed by folding the distal flap 76 before the ear panel 48 and the gasket cuff 70 are joined to each other through the elements constituting the chassis 54 such as a backsheet, a topsheet, and/or a barrier leg cuff. This allows easy and simple operation to fold the distal flap 76 since the ear panel 48 is not an obstacle to fold the distal flap 76 to form the gasket cuff 70. Therefore, it is preferable that the chassis 54 having the outer leg cuff 42 is first assembled and then the ear panel 48 is joined to the chassis 54 as shown in FIG. 13.

The embodiment shown in FIGS. 1-3 is a so-called taped diaper having the fastening tape 39 to form the closure of the diaper. Alternatively, a pair of the ear panels may be joined to the chassis at both the front waist region and the back waist region. The longitudinal side edges of the ear panels at the front waist region and at the back waist region may be joined by a seam such that the diaper forms a so-called pull-on diaper having one waist opening and two leg openings.

Although particular embodiments of the present invention have been illustrated and described, it would be apparent to those skilled in the art that various other changes and modifications can be made without departing from the spirit of the present invention. It is therefore intended to cover in the appended claims all such changes and modifications that are within the scope of this invention.

What is claimed is:

1. A disposable absorbent article comprising
a liquid pervious topsheet,
a liquid impervious backsheet,
an absorbent core disposed therebetween,
an elasticized outer leg cuff disposed adjacent to a longitudinal side edge of the absorbent article, the elasticized outer leg cuff having a base and a gasket cuff supported by the base at a joint of the base to the gasket cuff, the gasket cuff being provided with elasticity and having an inner cuff extending laterally inwardly from the joint and an outer cuff extending laterally outwardly from the joint, and
a barrier leg cuff having a proximal edge and a distal edge, the barrier leg cuff disposed inboard of the gasketing cuff, and the distal edge of the barrier leg cuff being spaced away from the top surface of the topsheet to form a pocket by a combination of the inner cuff, the base and the barrier leg cuff.

2. The disposable absorbent article of claim 1 wherein the elasticized outer leg cuff is generally T-shaped.

3. The disposable absorbent article of one of claims 1 and 2 wherein the proximal edge of the barrier leg cuff is positioned on the base of the elasticized outer leg cuff.

4. The disposable absorbent article of claim 3 wherein the inner cuff has an inner longitudinal edge, and the distance between the joint and the proximal edge of the barrier leg cuff is greater than the distance between the joint and the inner longitudinal edge of the inner cuff in a crotch region of the disposable absorbent article.

5. The disposable absorbent article of claim 4 wherein the distance between the joint and the proximal edge of the barrier leg cuff is-between about 5 mm and about 60 mm.

6. The disposable absorbent article of claim 4 wherein the outer cuff has an outer longitudinal edge, and the distance between the distal edge and the proximal edge of the barrier leg cuff is less than the distance between the proximal edge of the barrier leg cuff and the outer longitudinal edge of the outer cuff in a crotch region of the disposable absorbent article.

7. The disposable absorbent article of claim 6 wherein the distance between the joint and the proximal edge of the baffler leg cuff is greater than the distance between the distal edge and the proximal edge of the barrier leg cuff in a crotch region of the disposable absorbent article.

8. The disposable absorbent article of claim 7 wherein the distance between the distal edge and the proximal edge of the barrier leg cuff is less than the distance between the proximal edge of the barrier leg cuff and the inner longitudinal edge of the inner cuff in a crotch region of the disposable absorbent article.

9. The disposable absorbent article of claim 1 wherein the elasticized outer leg cuff is integrally formed with an extension of an element constructing the absorbent article.

10. The disposable absorbent article of claim 9 wherein the extension of the element constituting the absorbent article comprises an element selected from an extension of the topsheet, an extension of the backsheet, an extension of an outer nonwoven covering the backsheet, an extension of the barrier leg cuff, or combination thereof.

* * * * *

UNITED STATES PATENT AND TRADEMARK OFFICE
CERTIFICATE OF CORRECTION

PATENT NO. : 7,435,243 B2
APPLICATION NO. : 10/325153
DATED : October 14, 2008
INVENTOR(S) : Kouichi Miyamoto It is certified that error appears in the above-identified patent and that said Letters Patent is hereby corrected as shown below:

<u>Claim 5</u>

Col. 13, Line 3, after "is", delete "-".

<u>Claim 7</u>

Col. 14, Line 2, delete "baffler" and insert -- barrier --.

Signed and Sealed this

Eleventh Day of August, 2009

David J. Kappos
*Director of the United States Patent and Trademark Office*

UNITED STATES PATENT AND TRADEMARK OFFICE
CERTIFICATE OF CORRECTION

PATENT NO. : 7,435,243 B2
APPLICATION NO. : 10/325153
DATED : October 14, 2008
INVENTOR(S) : Kouichi Miyamoto It is certified that error appears in the above-identified patent and that said Letters Patent is hereby corrected as shown below:

<u>Claim 5</u>

Col. 13, Line 17, after "is", delete "-".

<u>Claim 7</u>

Col. 14, Line 2, delete "baffler" and insert -- barrier --.

This certificate supersedes the Certificate of Correction issued August 11, 2009.

Signed and Sealed this

First Day of September, 2009

David J. Kappos
*Director of the United States Patent and Trademark Office*